(12) United States Patent
Mills

(10) Patent No.: US 11,713,419 B2
(45) Date of Patent: Aug. 1, 2023

(54) SYSTEMS AND METHODS FOR PRODUCING LIGNOCELLULOSIC ALKANES

(71) Applicant: T.EN Process Technology, Inc., Houston, TX (US)

(72) Inventor: Kevin J. Mills, Yorba Linda, CA (US)

(73) Assignee: T.EN Process Technology, Inc., Houston, TX (US)

( * ) Notice: Subject to any disclaimer, the term of this patent is extended or adjusted under 35 U.S.C. 154(b) by 47 days.

(21) Appl. No.: 16/892,947

(22) Filed: Jun. 4, 2020

(65) Prior Publication Data
US 2021/0380885 A1    Dec. 9, 2021

(51) Int. Cl.
| | |
|---|---|
| *C10B 53/02* | (2006.01) |
| *C10B 47/00* | (2006.01) |
| *C10B 49/02* | (2006.01) |
| *C10B 51/00* | (2006.01) |

(52) U.S. Cl.
CPC .............. *C10B 53/02* (2013.01); *C10B 47/00* (2013.01); *C10B 49/02* (2013.01); *C10B 51/00* (2013.01)

(58) Field of Classification Search
CPC ..... C07C 1/20; C07C 9/22; C01B 2203/0233; C01B 2203/1241; C01B 3/34;
(Continued)

(56) References Cited

U.S. PATENT DOCUMENTS

| | | | |
|---|---|---|---|
| 4,431,509 A | 2/1984 | Tarman | |
| 5,961,786 A * | 10/1999 | Freel | C10B 49/22 208/126 |

(Continued)

FOREIGN PATENT DOCUMENTS

| | | |
|---|---|---|
| WO | 2009/018531 A1 | 2/2009 |
| WO | 2013134391 A1 | 9/2013 |
| WO | 2015104430 A1 | 7/2015 |

OTHER PUBLICATIONS

International search report and written opinion issued in corresponding PCT application No. PCT/US2021/035932, dated Sep. 23, 2021.
(Continued)

*Primary Examiner* — Ellen M McAvoy
*Assistant Examiner* — Chantel L Graham
(74) *Attorney, Agent, or Firm* — Locke Lord LLP; Alan B. Clement; Alicia J. Carroll

(57) ABSTRACT

A process for converting lignocellulosic feedstock includes providing a lignocellulosic feedstock into a first inlet of a first reactor at a first end, and providing a hot feedstock into a second inlet of the first reactor at a second end of the first reactor. The process includes heating and reacting the lignocellulosic feedstock with the hot feedstock and outputting a first product stream from a first product outlet of the first reactor. The first product stream is an alkane rich product stream. A reactor system includes a first reactor having a first inlet at a first end, a second inlet at a second end and at least one product outlet. The first reactor is configured to receive a lignocellulosic feedstock at the first inlet and a hot feedstock at the second inlet. The system includes a second reactor having a first inlet downstream from the at least one product outlet.

25 Claims, 8 Drawing Sheets

(58) Field of Classification Search
CPC ......... C10B 47/00; C10B 49/02; C10B 51/00; C10B 53/02; C10G 1/06
See application file for complete search history.

(56) References Cited

U.S. PATENT DOCUMENTS

| | | |
|---|---|---|
| 7,578,927 B2 | 8/2009 | Marker et al. |
| 8,303,676 B1 | 11/2012 | Weaver et al. |
| 8,696,775 B2 | 4/2014 | Weaver et al. |
| 9,023,243 B2 | 5/2015 | Weaver et al. |
| 9,254,461 B2 | 2/2016 | Weaver et al. |
| 9,382,482 B2 | 7/2016 | Weaver et al. |
| 9,561,956 B2 | 2/2017 | Weaver et al. |
| 9,698,439 B2 | 7/2017 | Weaver et al. |
| 9,890,332 B2 | 2/2018 | Weaver et al. |
| 9,944,857 B2 | 4/2018 | Dayton et al. |
| 10,005,961 B2 | 6/2018 | Weaver et al. |
| 2009/0227823 A1 | 9/2009 | Huber et al. |
| 2010/0105970 A1 | 4/2010 | Yanik et al. |
| 2010/0162625 A1* | 7/2010 | Mills ............... C10K 1/028 422/187 |
| 2011/0277378 A1* | 11/2011 | Von Hebel ............... C10L 1/04 549/415 |

OTHER PUBLICATIONS

Dutta et al., "Process Design and Economics for the Conversion of Lignocellulosic Biomass to Hydrocarbon Fuels Thermochemical Research Pathways with In Situ and Ex Situ Upgrading of Fast Pyrolysis Vapors," National Renewable Labs, NREL/TP-5100-62455, Mar. 2015.

Xia et al., "Direct Hydrodeoxygenation of Raw Woody Biomass Into Liquid Alkanes," Nature Communications, 7:11162, DOI: 10.1038/ncomms11162 (Mar. 30, 2016).

Cao et al., "Application of Biochar-Based Catalysts in Biomass Upgrading: A Review," RSC Adv., 2017, 7, 48793-48805 (Oct. 16, 2017).

Granados et al., "Detailed Investigation into Torrefaction of Wood in a Two-Stage Inclined Rotary Torreer," Energy Fuels 2017, 31, 647658 (Nov. 25, 2016).

Zheng et al., "Effect of the Torrefaction Temperature on the Structural Properties and Pyrolysis Behavior of Biomass," BioResources 12(2), 3425-3447, bioresources.com (2017).

U.S. Department of Energy. 2011. U.S. Billion-Ton Update: Biomass Supply for a Bioenergy and Bioproducts Industry. R.D. Perlack and B.J. Stokes (Leads), ORNL/TM-2011/224. Oak Ridge National Laboratory, Oak Ridge, TN. 227p.

Zacher et al., "DOE Bioenergy Technologies Office (BETO) 2015 Project Peer Review: 2.3.1.302 Bio-oil Quality Improvement and Catalytic Hydrotreating of Bio-oils—PNNL", Pacific Northwest National Laboratory, Mar. 24, 2015.

Chowdhury et al., "Comparative Evaluation of Physiochemical Properties of a Solid fuel Derived from Adansonia digitata Trunk using Torrefaction," BioResources 12(2), 3816-3833, Apr. 12, 2017.

* cited by examiner

SYSTEMS AND METHODS FOR PRODUCING LIGNOCELLULOSIC ALKANES

BACKGROUND

1. Field

The present disclosure relates to conversion of lignocellulosic feedstocks, specifically conversion of lignocellulosic feedstocks to into primarily $C_{10}$ to $C_{24}$ alkanes (blends for diesel fuels).

2. Description of Related Art

Fuels formed from renewable sources, particularly biological sources (i.e., "biofuels"), are being sought and developed. Traditionally, biofuels, such as ethanol, are produced largely from grains. But another option for producing biofuel is with plant biomass exists in the form of lignocellulosic material. Conversion of lignocellulose to biofuel tends to be more difficult than the conversion of grain. Lignocellulosic materials (biomass) are oxygenated solid polymers, which have three primary structural components: cellulose, hemicellulose, and lignin. Nearly two-thirds of the lignin carbon is associated with unsaturated $C_6$ ring compounds. These compounds are very stable when compared to the remaining lignin structure. This is why pyrolyzed lignin has high hydrogen concentration.

One process that converts feedstock into gaseous, solid, and liquid products through the heating of biomass in the absence of oxygen is pyrolysis. Pyrolysis for producing liquid transportation fuels from biomass is described in U.S. Pat. No. 9,944,857 to Dayton et al. Residence times for fast pyrolysis are on the order of seconds, for example 5 seconds or less, as described in Dayton et al. However, flash pyrolysis is less than 0.5 seconds and slow pyrolysis is considered greater than 5 minutes. Typical liquefaction of biomass by pyrolysis occurs near 400° C. to 450° C. with an approximately 1 second residence time prior to quench cooling have resulted in 60% to 70% liquid yields by mass. However, the resulting liquids still have very high oxygen contents (greater than 20% by mass), and will continue to reform polymers, increasing in viscosity with age, both of which are generally undesirable to firing in diesel engines. Biomass fast pyrolysis also has energy efficiencies of 70% and greater. To make the resulting liquids appropriate for use in diesel engines, e.g. to remove the oxygen from the resulting liquids, typical approaches have been to conduct post-pyrolysis treatment of pyrolysis oils and/or catalytic approaches, for example.

Attempts have been made to deoxygenate thermal pyrolysis products to produce hydrocarbons, more importantly alkanes. The main areas of research have centered around hydrogen treatment of pyrolyzing lignocellulosic feedstocks, thermal pyrolytic treatment of blends of lignocellulosic feedstocks and catalysts, pyrolysis followed by catalytic treatment of the gas stream, catalytic upgrading of pyrolysis oils, treating either lignocellulosic feedstocks or pyrolysis oils in a supercritical atmosphere with either catalysts or reactants, and treatment (acid, base, and steam) for the purposes of separating of cellulose, hemicellulose, and lignin to facilitate processing to chemicals (some of which are alkanes). These deoxygenate treatments and processes tend to exhibit low effectiveness, low yields, and/or they can be expensive.

The hemicellulose material volatizes at temperature between 200° C. to 320° C. (peaking near 295° C.), cellulose between 300° C. to 380° C. (peaking near 345° C.), and lignin has a tendency to begin to volatize off very slowly at around 180° C. (peaking near 400° C.) and continues until it is completely char. After rapidly quenching the pyrolysis vapors and aerosols, three product phases are formed. The yields of each phase depend on the operating conditions, reactor design and feedstock characteristics, including ash content and the relative amounts of cellulose and lignin. The products phases are: fast pyrolysis liquid, solid char and non-condensable gas. Fast pyrolysis liquid is also known as bio-oil and pyrolysis oil and is obtained after vapor condensation. Biooil is black or dark brown and free flowing at room temperature and typically contains less than 30% of water and hundreds of oxygenated components. Bio-oil is mostly immiscible in hydrocarbon liquids and can be upgraded by hydrotreating to lower the oxygen content and decrease hydrophilicity. Solid char is primarily composed of carbon and is separated from the fast pyrolysis vapors and aerosols by cyclone. Solid char product can be used as fuel. Non-condensable gas typically is collected during vapor condensation. The gas is usually recycled internally as fluidizing gas for the fast pyrolysis reactor and/or collected for fuel use. The National Renewable Labs (NREL) has been developing pyrolysis to hydrocarbon fuels feasibility studies as part of the U.S. Department of Energy's Bioenergy Technologies Office's efforts to enable the development of technologies for the production of infrastructure compatible, cost-competitive liquid hydrocarbon fuels from biomass. NREL is developing refinery type hydrogenation, hydrodeoxygenation, and coupling biomass to alkanes reactions systems based on integrated dual vessel reactor and char combustor with an common heat carrier. The NREL in-situ technology utilizes a catalyst based heat carrier, while the ex-situ technology utilizes catalytic upgrading of the pyrolysis gases. More detail can be found in "Process Design and Economics for the Conversion of Lignocellulosic Biomass to Hydrocarbon Fuels Thermochemical Research Pathways with In Situ and Ex Situ Upgrading of Fast Pyrolysis Vapors," Dutta et al., National Renewable Labs, NREL/TP-5100-62455, March 2015.

Traditional biomass flash pyrolysis processes have demonstrated a roughly 70% liquid product yield; however, this pyrolysis oil product has limited use without additional upgrading or refining. Other biomass to alkanes processes catalytically treat pyrolysis gases with char or other carbon based catalysts. U.S. Pat. No. 9,382,482 to Weaver, et al, describes methods, systems, and devices for continuous fuel production. Some embodiments may utilize two pyrolysis platforms, which may utilize biomass as a feedstock. One platform may generally utilize a high temperature pyrolysis process that may generate at least hydrogen and carbon monoxide. WO2015104430A1 to Schulzke et al. bring in contact the pyrolysis gases and the process char and other carbon based catalysts, at a temperature between 450° C.-600° C., preferably, 500° C.-550° C.

Biomass pyrolysis is the thermal depolymerization of biomass at modest temperatures in the absence of added oxygen to produce a mixture of solid, liquid, and gaseous products depending on the pyrolysis temperature and residence time. Charcoal yields of up to 40% can be achieved for slow pyrolysis at low temperature, high pressure, and long residence time. Flash pyrolysis is used to optimize the liquid products as an oil known as bio-crude or bio-oil. High heating rates and short residence times enable rapid biomass pyrolysis while minimizing vapor cracking to optimize liquid product yields with up to about 70% efficiency on a weight basis. Bio-oil can be upgraded either at the source prior to full production or after the formation of the liquid product. To date, the two most popular methods in post-production upgrading are adapted from traditional hydrocarbon processing. These processes are bio-oil cracking over solid acid catalysts and hydrotreating in the presence of high pressure hydrogen and a hydrodesulfurization (HDS) catalyst. Although both of these processes have the potential to lower the oxygen content to a desirable level, it should be noted that both cracking and hydrotreating are accompanied by the loss of hydrogen (as $H_2O$) and carbon (as $CO_2$ or CO) from the bio-oil.

Similar to petroleum crude oil processes, key issues such as coke deposition and catalyst stability still remain for biomass processing or bio-crude upgrading over the conventional catalysts. In some cases, the conventional catalysts may no longer be suitable for bio-crude or biomass processing. Using dehydration of a fast pyrolysis bio-oil to achieve removal of oxygen (the main product of hydrodeoxygenation (HDO) and cracking over acid catalysts) would require over 80% of the hydrogen in the bio-oil if no external hydrogen were supplied. A number of analyses reveal that upgrading of bio-crude through hydrotreating is not economically attractive because of the high demand of hydrogen. It can also be seen that similar issues may occur in the upgrading of bio-crude through conventional cracking over acid catalysts. Therefore, conventional methodologies such as hydrotreating and cracking do not allow higher efficiencies to be achieved during the conversion of biomass to upgraded bio-oil.

Xia, et al. describes a technique whereby using a multifunctional $Pt/NbOPO_4$ catalyst, raw woody biomass can be directly converted into liquid alkanes in high yields in a single-phase medium (cyclohexane) with cellulose, hemicellulose and lignin fractions in solid woods being converted into hexane, pentane and alkylcyclohexanes, respectively. Xia et al., "Direct Hydrodeoxygenation of Raw Woody Biomass Into Liquid Alkanes," NATURE COMMUNICATIONS, 7:11162, DOI: 10.1038/ncomms11162 (Mar. 30, 2016). Furthermore, Cao et al. describes methods in which biochars could be produced at high temperatures to be used as biochar-based catalysts for biodiesel production, and biochars as catalyst supports for biomass pyrolysis, gasification, and bio-oil upgrading. Cao et al., "Application of Biochar-Based Catalysts in Biomass Upgrading: A Review," RSC Adv., 2017, 7, 48793-48805 (Oct. 16, 2017).

Granados et al. describes a two-stage, inclined continuous rotary torrefier, processes for improving biomass torrefaction at 280° C., and investigates the effect of temperature and residence time on the properties of torrefied biomass. Granados et al., "Detailed Investigation into Torrefaction of Wood in a Two-Stage Inclined Rotary Torrefier," Energy Fuels 2017, 31, 647-658 (Nov. 25, 2016). Zheng et al. shows that the large number of pores that formed on the surface of the sample, increasing overall surface area, was due to the release of volatile compounds during pyrolysis. Zheng et al., "Effect of the Torrefaction Temperature on the Structural Properties and Pyrolysis Behavior of Biomass," BioResources 12(2), 3425-3447, bioresources.com (2017).

The conventional techniques have been considered satisfactory for their intended purpose. However, there is an ever present need for improved systems and methods which can economically convert lignocellulosic feedstocks into a drop-in diesel fuel at an industrial scale. This disclosure provides a solution for this need.

SUMMARY

A process for converting lignocellulosic feedstock into an alkane rich product includes providing a lignocellulosic feedstock into a first inlet of a first reactor at a first end of the first reactor and providing a hot feedstock into a second inlet of the first reactor at a second end of the first reactor. The process includes heating and reacting the lignocellulosic feedstock with the hot feedstock. The process includes outputting a first product stream from a first product outlet of the first reactor, wherein the first product stream is an alkane rich product stream.

In accordance with some embodiments, heating and reacting the lignocellulosic feedstock includes heating the lignocellulosic feedstock over a period ranging from 10 seconds to 20 minutes, preferably from 30 seconds to 2 minutes, at temperatures up to 400° C. Reacting the lignocellulosic feedstock with the hot feedstock includes a deoxygenation reaction between at least one of hydrogen (H2) or carbon monoxide (CO), and polysaccharides. The hot feedstock can be a hydrogen rich gas stream. The process can include outputting a second product from a second product outlet of the first reactor and feeding the second product into a second reactor. The second product can include a volatile solid. The process can include heating the second product in the second reactor to a temperature over 700° C. resulting in a hot high-hydrogen concentration gas stream and an unused solids stream.

It is contemplated that the process can include releasing the hot high-hydrogen concentration gas stream from the second reactor into the second inlet of the first reactor to provide at least a portion of the hot feedstock. The process can include discharging the unused solids stream from the second reactor. The process can include distilling the first product stream into an alkane rich liquid, aromatics, water, and gases. Thirty to fifty percent of the alkane rich liquid of the first product stream can include $C_{18}$ alkanes. Thirty to forty percent of the alkane rich liquid of the first product stream can include $C_{16}$ and $C_{17}$ alkanes. The first reactor can be a counter-flow reactor configured and adapted to providing the hot feedstock in a counter-flow orientation relative to the lignocellulosic feedstock.

The process can include cooling the hot feedstock with a thermal controller prior to providing the hot feedstock to the first reactor to minimize explosive cracking of polymers of the lignocellulosic feedstock. The process can include providing at least one of a recycled gas stream or a steam stream to the second reactor. The process can include pre-heating the lignocellulosic feedstock to a temperature up to 180° C. with a heater prior to providing the lignocellulosic feedstock to the first reactor. The process can include venting volatiles from the heater to a position downstream from the first product outlet of the first reactor. The process can include providing hydrogen to the first reactor at a position downstream from the second inlet of the first reactor. The process can include reacting methane and water vapor with a methane cracker to generate hydrogen and carbon monoxide products upstream from the second inlet of the first reactor.

In accordance with another aspect, a reactor system for converting lignocellulosic feedstock into an alkane rich product includes a first reactor having a first inlet at a first end, a second inlet at a second end and at least one product outlet. The first reactor is configured and adapted to receive a lignocellulosic feedstock at the first inlet and a hot feedstock at the second inlet. The system includes a second reactor having a first inlet downstream from the at least one product outlet of the first reactor to receive a product therefrom.

In some embodiments, the second reactor includes a first product outlet upstream from and in fluid communication with the second inlet of the first reactor to provide a hot high-hydrogen concentration gas stream thereto. The second reactor can include a second product outlet configured and adapted to discharge an unused solids stream from the second reactor. The first reactor can be a counter-flow reactor configured and adapted to provide a hot feedstock in a counter-flow orientation relative to a lignocellulosic feedstock.

A thermal controller can be downstream from a first product outlet of the second reactor. The thermal controller can be between the second reactor and the second inlet of the first reactor. The second reactor can include a second inlet upstream from the first product outlet. The second inlet can be configured and adapted to receive at least one of a recycled gas stream or a steam stream. The system can include a heater upstream from the first inlet of the first reactor configured and adapted to pre-heat a lignocellulosic feedstock. The heater can include a vent in fluid communication with the at least one product outlet of the first reactor configured and adapted to vent any potential volatiles stream.

In some embodiments, the system includes third reactor downstream from the second reactor. The third reactor can include a first inlet in fluid communication with a second product outlet of the second reactor to receive an unused solids stream therefrom. The third reactor can include a first output in fluid communication with the first reactor via a third inlet of the first reactor to provide hydrogen thereto. It is contemplated that the system can include a methane cracker downstream from a first product outlet of the second reactor. The methane cracker can be between the second reactor and the second inlet of the first reactor.

These and other features of the embodiments of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1:
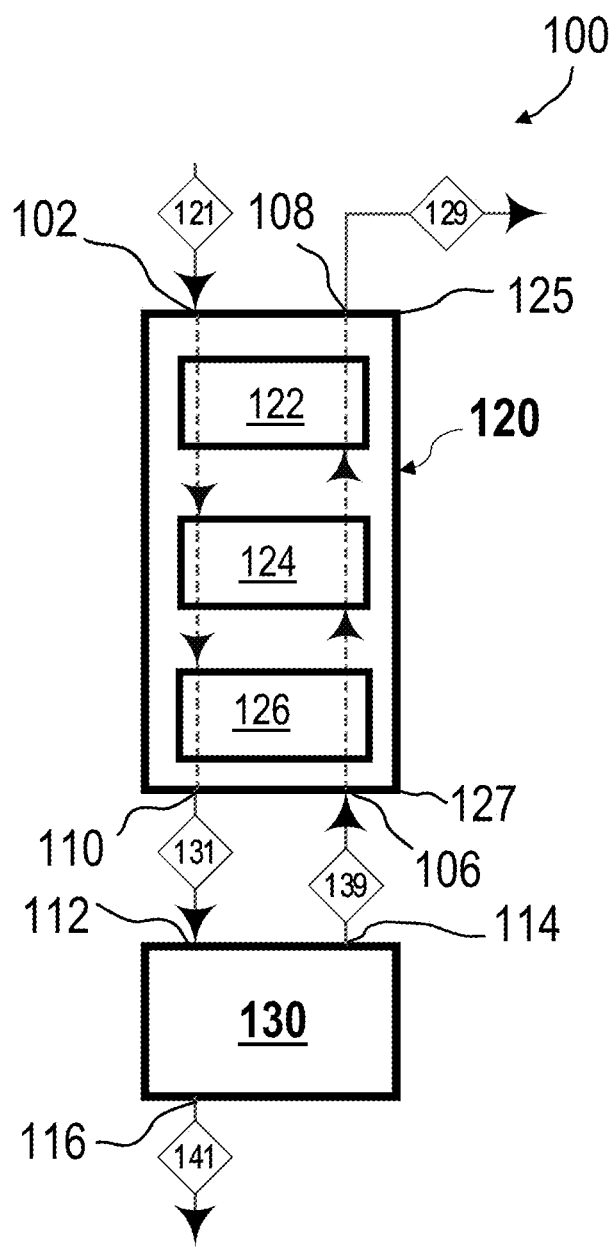
FIG. 1 is a schematic depiction of an embodiment of a reactor system for converting lignocellulosic feedstock into an alkane rich product constructed in accordance with the present disclosure, showing a first reactor with a first product stream output and a second reactor.

Reference will now be made to the drawings wherein like reference numerals identify similar structural features or aspects of the subject disclosure. For purposes of explanation and illustration, and not limitation, an illustrative view of an embodiment of a system for converting lignocellulosic feedstock into an alkane rich product is shown in FIG. 1 and is designated generally by reference character 100. Other embodiments of systems in accordance with the disclosure, or aspects thereof, are provided in FIGS. 2-10, as will be described. Embodiments described herein can be used to provide systems and processes for generating an economic, drop-in diesel fuel which meets Department of Transportation and Environmental Protection Agency standards for Advanced Lignocellulosic Diesel. Economically is defined as production cost including feedstock, levelized capital, operating and maintenance costs, plus green value being greater than the price of crude oil plus the crack spread on a per gallon basis.

As shown in FIG. 1, a reactor system 100 for converting a lignocellulosic feedstock 121 into a first product stream 129, e.g. an alkane rich product stream, includes a first reactor 120 having a first inlet 102 to receive lignocellulosic feedstock 121 at a first end 125, e.g. a cold end. The temperature of lignocellulosic feedstock 121 at input ranges from ambient temperature to 180° C. In some embodiments, feedstock 121 is input at a temperature ranging from 100-150° C., or preferably 125-150° C. First reactor 120 includes a second inlet 106 at a second end 127, e.g. a hot end, where the term "hot end" is used relative to the "cold end." The temperature across first reactor 120 ranges from 180° C. (at cold end 125) up to 750° C. (at hot end 127), preferably up to 550° C. at hot end 127. First reactor 120 includes a first product outlet 108, e.g. product gas outlet 108, and a second product outlet 110. First reactor 120 is a counter-flow reactor configured and adapted to receive a hot feedstock 139, e.g. a hot high-hydrogen concentration gas stream, in a counter-flow orientation relative to lignocellulosic feedstock 121, e.g. a dry biomass, at temperatures suitable to forming alkanes. In some embodiments, reactor 120 is sized to process 500 tons of lignocellulosic feedstock 121 per day at 10 atm, e.g. it can be approximately 12-14 feet in diameter.

With continued reference to FIG. 1, a variety of reactors can be used for first reactor 120, e.g. a moving bed, a fixed bed, a riser reactor, a transport reactor, a bubbling fluidized bed, circulating fluidized beds, a Winkler reactor and/or an auger reactor, or another suitable reactor. First reactor 120 is configured and adapted to receive hot feedstock 139 at the second inlet 106. Hot feedstock 139 is provided into reactor 120 at second inlet 106 at a temperature ranging from 450° C. to 750° C., preferably 550° C. The longer the residence time, the lower the hot feedstock 139 temperature can be. The temperature of hot feedstock 139 may also vary depending on the heat duty for the mass of gas provided. In other words, with more mass at inlet 106, a lower temperature (e.g. 550° C.) may be used. Lignocellulosic feedstock solids 121 progress to hot end 127 of first reactor 120 resulting in high conversion efficiencies to diesel-typical carbon number alkanes ($C_5$-$C_{24}$) which make up first product stream 129. First product stream 129 is made of product gases that flow towards the cold end of first reactor 120 and exit from first product outlet 108. After exiting reactor 120, first product stream 129 is distilled with a distillation column (not shown) into an alkane rich liquid, aromatics, water, and gases, without requiring further post-reactor processing (e.g. further oxygen removal via post-pyrolysis treatment of pyrolysis oils and/or catalytic approaches).

First product stream 129 exits first product outlet 108 at a temperature ranging from 200° C.-300° C. As dry biomass 121 progresses from cold end 125 to hot end 127 of first reactor 120, the gases and vapors percolate through dry lignocellulosic feedstock solids 121 in a counter-flow orientation from the hot end 127, at the entry of hot high-hydrogen concentration gas stream 139 from the second reactor 130, to the cold end 125, at the exit of first product stream 129. The counter-flow orientation allows for an intermediate heat up rate/ramp of feedstock 121, resulting in more stable reactions. This stability allows for low structural damage of the lignin based skeleton, thereby allowing the reacting biomass 121 to also act as a catalyst, negating the need to treat pyrolysis solids to form a catalyst.

With continued reference to FIG. 1, first reactor 120 is operated in a pressure range from 1 atm to 20 atm. In some embodiments, for example, first reactor is operated between 1 and 10 atm. As shown by the chart 500 in FIG. 10, in accordance with embodiments of the present disclosure, it has been found that higher pressures in first reactor 120 result in HDO reactions having an increased alkane yields. However, there is a diminishing return as the pressure exceeds 10 atm, making the higher pressure and higher yield a trade-off with the ease and feasibility of maintaining pressures over 10 atm within first reactor 120. Higher pressures, such as 10 atm, tend to reduce the velocity of the counter flow gases, including stream inlet gases 139 at the hot end 106 through to the product gases 129 at the cold end 125 of the first reactor 120.

As shown in FIG. 1, system 100 includes a second reactor 130 having a first inlet 112 downstream from second product outlet 110 of the first reactor to receive a product 131 therefrom. Product 131 exits first reactor 120 at a temperature ranging from 350° C. to 500° C., preferably between 380° C.-400° C. Product 131 contains volatiles which are released in the hot end of first reactor 120, in the high hydrogen and carbon monoxide atmosphere in the presence of the remaining catalytically reactive ligno-skeleton. This results in additional alkanes and alkane pre-cursors, which flow to cold end 125 and exit as product gases 129. The heat for first reactor 120 is provided by way of the combustion of the waste char, the distillation overs, or lignocellulosic materials via heat materials (e.g. recirculated sand, recirculated mineral powders, etc.), which are contained within product 131, in the second reactor 130 (or in a third reactor 140, depending on the embodiment). In embodiments where second reactor 130 is not present, the external heat may be supplied by combustion of fossil or other renewable fuels, or by electric conduction.

With continued reference to FIG. 1, tars and high molecular weight gases condense onto the feed biomass at cold end 125 of a reactor. The remaining unreacted high volatile char is output from the first reactor 120 as product 131 at second product outlet 110 and used as the feedstock to make the hydrogen rich pyrolysis gases 139 in second reactor 130. Second reactor 130 includes a first product outlet 114 upstream from and in fluid communication with second inlet 106 of first reactor 120 to provide hot high-hydrogen concentration gas stream 139 thereto. The second reactor 130 is heated and held to a temperature greater than 700° C., preferably 750° C. Those skilled in the art will readily appreciate that, in some embodiments, second reactor 130 may not be included and, instead, first reactor 120 is connected to an alternative source (or sources) for hot high-hydrogen concentration gas stream 139. Second reactor 130 includes a second product outlet 116 to discharge an unused solids stream 141 from second reactor 130.

As shown in FIG. 1, a process for converting lignocellulosic feedstock into an alkane rich product includes providing a lignocellulosic feedstock, e.g. feedstock 121, into a first inlet, e.g. first inlet 102, of a first reactor, e.g. first reactor 102, at a first end, e.g. first end 125, of the first reactor. The process includes providing a hot feedstock, e.g. a hot high-hydrogen concentration gas stream, such as hot feedstock 139, into a second inlet, e.g. second inlet 106, of the first reactor at a second end, e.g. second end 127, of the first reactor. The remainder of the high-hydrogen concentration stream 139 is mainly carbon-monoxide and carbon-dioxides. The process includes heating and reacting the lignocellulosic feedstock with the hot feedstock. The process includes outputting a alkane rich product stream, e.g. first product stream 129, from a first product outlet, e.g. the first product outlet 108, of the first reactor. In some embodiments, the process includes conducting the reaction at increased pressure, e.g. 10 atm. This increased pressure may increase yield of product stream 129 by 20-25% per ton of biomass 121.

The process described above allows for mechanical equipment, controls or hydraulic enhancements to prevent the high volatile char from agglomerating into a harden mass due to tars and waxes coking. The process allows for incorporation of vibratory grids across any sections of falling solids/updraft type reactors to prevent solids from bridging. The process incorporates constant temperature chaining reactor to maximize yields. It is also contemplated that the process can include a double effect dryer to control feedstock moisture. Reaction kinetics as they relate to active ash elements (e.g. iron, potassium, etc.) can be explored to further improve the process. Similarly, char from stream 131 can be burned externally for the purposes of producing an ash and potentially a High Carbon Chaining Reaction catalyst. In some embodiments, it is contemplated that the process can include incorporating a hydrocarbon chaining reaction type (FT) catalysts blended with biomass, burn off tars and remaining char externally for the purposes of producing an ash and potentially a High Carbon Chaining Reaction Catalyst.

In some embodiments, it is contemplated that the process can include injecting $CH_4$ (Natural Gas) into the second reactor 130 for increased carbon monoxide and hydrogen. It is assumed, although fossil, that natural gas is cheaper than diesel on a value/energy basis, used as a means of improving the incremental economics. Other "green" fuels can also be used. In some embodiments, it is contemplated that the process can include incorporating waste lignin injection into the high temperature or carbon reactor for increased carbon monoxide and hydrogen for the alkane chaining reaction. Waste lignin would most probably have a sulfur component that would be have to be considered in the process design. In accordance with another aspect, Calcined Ash can be used as a feedstock of the biomass fertilizer, the fertilizer should have the proper iron and alkali for the soil to optimize the catalytic activity of the biomass feed ash.

Those skilled in the art will readily appreciate that the distillation process, downstream from product gas outlet 108, can include $C_6$ Ring Azeotrope to Alkane separation. It is also contemplated that a pressurized oxygen waste water stripping step can be used to remove organics from the waste water. In some embodiments, a waste heat valued stream fired steam power cycle can be used. Steam stripping can be used to remove organics from the waste water as the steam cycle condenser. In some embodiments, a catalyst can be mixed with hot high-hydrogen concentration gas stream 139. The process can include controlling the hydrogen distribution in the HDO zone, zone 124, blending of coarse sand or other inert materials with the hot high-hydrogen concentration gas stream 139 to aid in hydraulics, and/or reincorporating upgraded ash as a reactor catalyst. It is also contemplated that temperature controlled and near isothermal reactors can be used. An external Fischer-Tropsch (FT) reactor can be used for unused streams.

Figure 2:
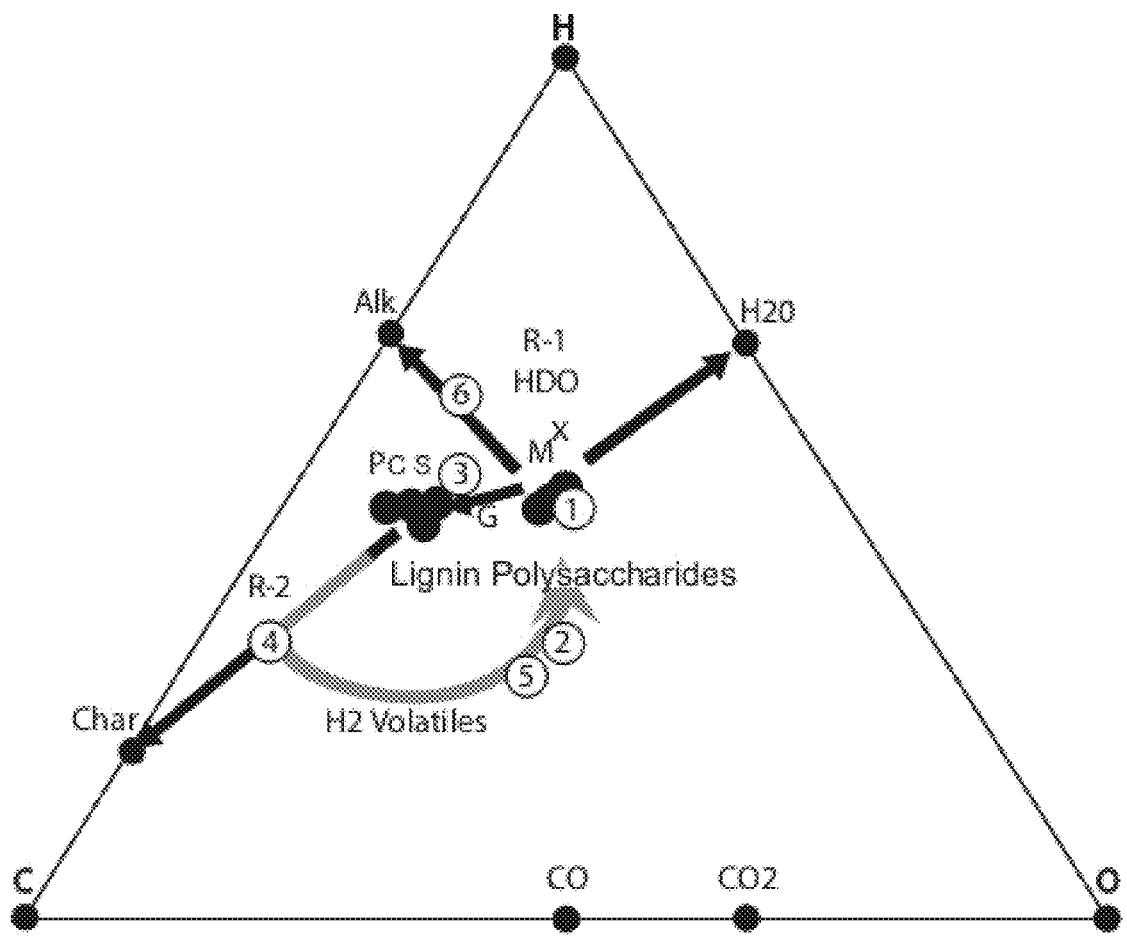
FIG. 2 is a graphical depiction of the process sequence chemistry for the first and second reactors, showing the outputs from the first and second reactors.
Figure 3:
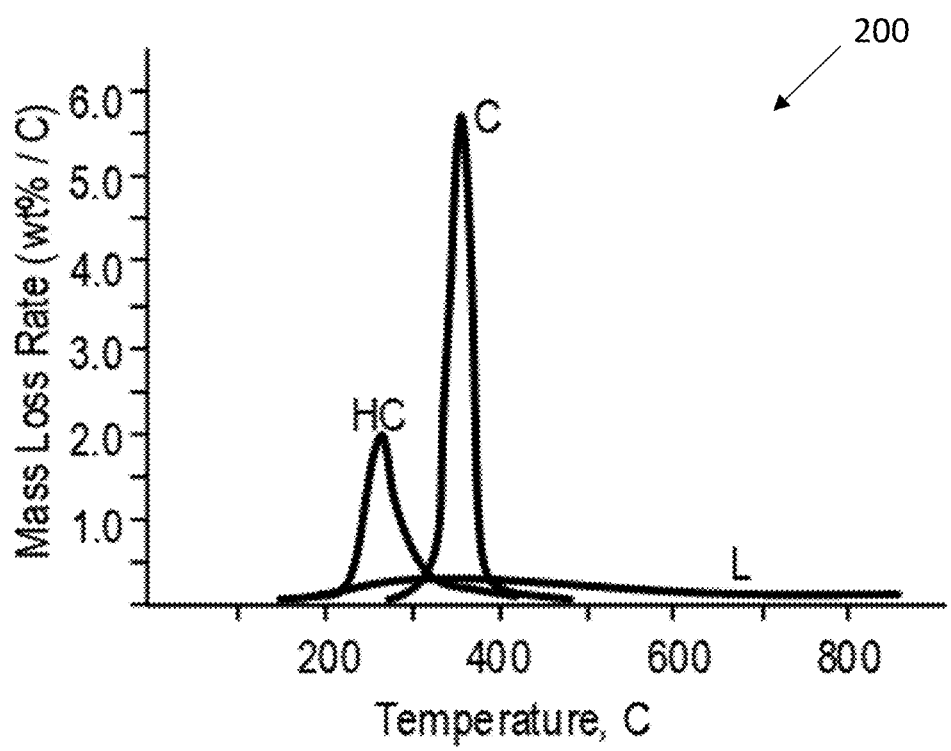
FIG. 3 is thermal gravimetric analysis (TGA) of lignocellulosic components: hemicellulose (HC), cellulose (C), and lignin (L), showing that the hemicellulose materials are volatilized at low temperatures, then cellulose, and lignin are volatized along the complete temperature range (100°-900° C.)

With reference now to FIGS. 1-3, heating and reacting lignocellulosic feedstock 121 includes heating lignocellulosic feedstock 121 over a period ranging from 10 seconds to 20 minutes at temperatures up to 400° C. Depending on the position of lignocellulosic feedstock 121 within first reactor 120, its temperature range within reactor 120 ranges from 180-400° C. In some embodiments, the temperature range for lignocellulosic feedstock 121 can be up to 450° C. The process includes outputting a second product, e.g. a volatile solid product 131, from a second product outlet, e.g. second product outlet 110, of the first reactor and feeding the second product into a second reactor, e.g. second reactor 130. The process includes heating the second product in the second reactor to a temperature over 700° C. resulting in a hot high-hydrogen concentration gas stream, e.g. gas stream 139, and an unused solids stream, e.g. unused solids stream 141. The process includes releasing the hot high-hydrogen concentration gas stream from the second reactor into the second inlet of the first reactor to provide at least a portion of the hot feedstock. The process includes distilling the first product stream 129 into an alkane rich liquid, aromatics, water, and gases. Once distilled, 30%-50% of the alkane rich liquid of product stream 129 contains $C_{18}$ alkanes, and, combined, $C_{16}$ and $C_{17}$ alkanes comprise 30%-40% of the alkane rich liquid.

As shown in FIG. 2, a summary of the process sequence chemistry is schematically shown. At (1) lignocellulosic materials 121 are fed into first reactor R-1/120. This material is heated and reacted at (2) with the volatiles released from the second reactor R-2/130, over a 10 second to 20 minute solids residence time up to about 400° C. to produce a high-volatile-char 131 at (3) completing the volatizing and reacting of the polysaccharides ($C_5$ and $C_6$ sugars). High-volatile-char 131 is moved to second reactor 130/R-2 where it is rapidly heated at (4) to over 700° C. Those skilled in the art will appreciate that the temperature in second reactor 130 can be adjusted higher to make heat balance with the required first reactor thermal treated duty. When high-volatile char (3)/131 is heated at (4), within second reactor 130, high temperature hot high-hydrogen concentration volatiles 139 are released at (5). These volatiles 139 are used to heat lignocellulosic materials 121 in first reactor 120 in a counter flow orientation, as previously described above. The hydrogen in hot high-hydrogen concentration gas stream 139 react with lignocellulosic materials 121 in a series of hydrogen deoxygenation reaction steps to produce an alkanes rich product gas 129 at (6).

As shown in FIG. 3, an example thermal gravimetric analysis (TGA) of lignocellulosic components (hemicellulose (HC), cellulose (C), and lignin (L)) is provided. TGA analysis 200 shows that hemicellulose materials are volatilized at low temperatures, then cellulose, and lignin is volatized along the complete temperature range (100° C.-900° C.). In some examples, it has also been seen that when a TGA is conducted at its high end, 50° C./minute, there are lower chars compared to TGAs conducted at 1° C./minute (40% of raw weight versus 30% of raw weights). Furthermore, it should be noted that both of the mass yields are higher than what laboratory compositional analysis has measured. Therefore, there is likely some cellulose and hemicellulose components which remain within the lignin skeleton.

Figure 4:
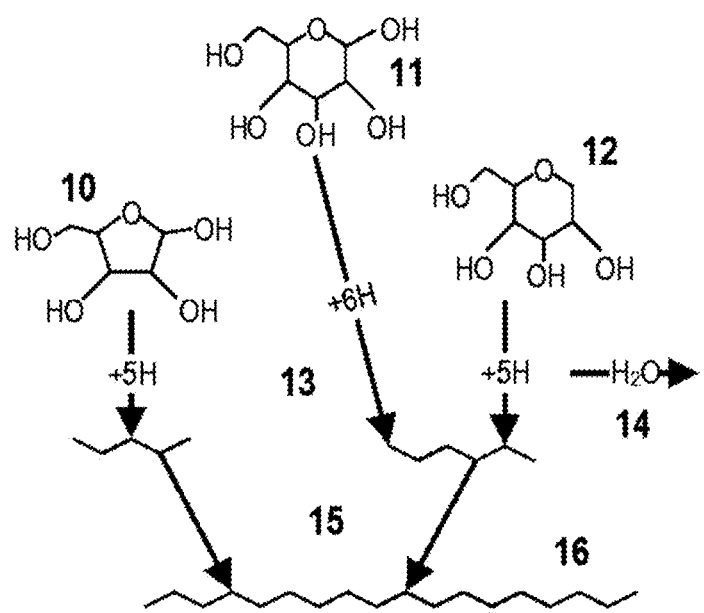
FIG. 4 is a schematic graphical depiction of a summary of cellulose hydrogen deoxygenation (hydrodeoxygenation, HDO) to hexane.

With reference now to FIG. 4, a summary of cellulose hydrogen deoxygenation (hydrodeoxygenation, HDO) to hexane in accordance with embodiment of the present disclosure is shown. The cellulose and hemi-cellulose materials consist of polymer strings of $C_5$ 10 and $C_6$ 11 hemicellulose and $C_6$ cellulose (glucose) 12, sugars called polysaccharides. Polysaccharides are more reactive with hydrogen than lignin due to their volatile activity between 180°-400° C. Whereas, lignin is much more stable through these temperature regions. Polysaccharide and hydrogen reactions 13 include hydrogenation, hydrogenolysis, hydrodeoxygenation, isomerization, and dehydration. Hydrogenation is a chemical reaction that occurs between molecular hydrogen ($H_2$) and another chemical species. Hydrogenolysis is a cleavage reaction in which the hydrogen molecule ($H_2$) reacts with an organic compound resulting in two small compounds. Hydrodeoxygenation is a hydrogenolysis process for removing oxygen from oxygen containing compounds. A dehydration reaction is a chemical reaction between two compounds where one of the products is water. For example, two monomers may react where a hydrogen (H) from one monomer binds to a hydroxyl group (OH) from the other monomer to form a dimer and a water molecule ($H_2O$). There is an abundance of water formed during these reactions 14. Once the pentanes 10 and hexanes 11 are formed, they chain up 15 to form longer alkane chains 16. (e.g. $C_{15}$-$C_{18}$, as part of first product stream 129). The following are some of the prominent reactions occurring in reactor 120 in accordance with the present disclosure:

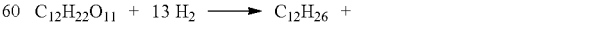
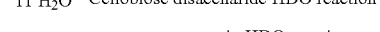
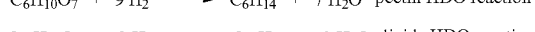
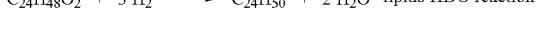

$C_5H_{10}O_5 + 6\,H_2 \longrightarrow C_5H_{12} + 5\,H_2O$  $C_5$ saccharide HDO reaction $C_6H_{12}O_6 + 7\,H_2 \longrightarrow C_6H_{14} + 6\,H_2O$  $C_6$ saccharide HDO reaction $C_{12}H_{22}O_{11} + 13\,H_2 \longrightarrow C_{12}H_{26} +$ $11\,H_2O$  Cellobiose disaccharide HDO reaction $C_6H_{10}O_7 + 9\,H_2 \longrightarrow C_6H_{14} + 7\,H_2O$  pectin HDO reaction $C_{24}H_{48}O_2 + 3\,H_2 \longrightarrow C_{24}H_{50} + 2\,H_2O$  lipids HDO reaction Additionally, as the partial pressure of hydrogen is reduced (consumed) during the HDO reaction process, carbon monoxide can also begin to react with the polysaccharide oxygen molecules, especially when the oxygen atom not associated with an OH group. When this occurs, a carbon-dioxide molecule is formed and volatilize instead a water molecule (FIG. 4 only shows HDO reactions).

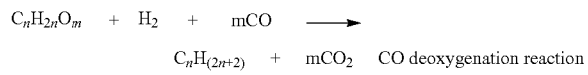

CO deoxygenation reaction

The reactions shown above, in certain embodiments the speed of the reactions take place over ten seconds to several minutes and occur between 180° C.-400° C. depending on the overall specific characteristics of lignocellulosic material 121 (the composition of cellulose, hemi-cellulose and type, and lignin and type changes from plant to plant type).

The volatile release in the hot end, e.g. a tar cracking zone 126, of first reactor 120, in the high hydrogen and carbon monoxide atmosphere and in the presence of the remaining catalytically reactive ligno-skeleton results in additional alkanes and alkane pre-cursors, which then flow towards the cold end of the first reactor 120. Generally, tar cracking zone 126 of first reactor 120 ranges from 350° C. to 500° C., preferably between 380° C.-400° C.

Figure 5:
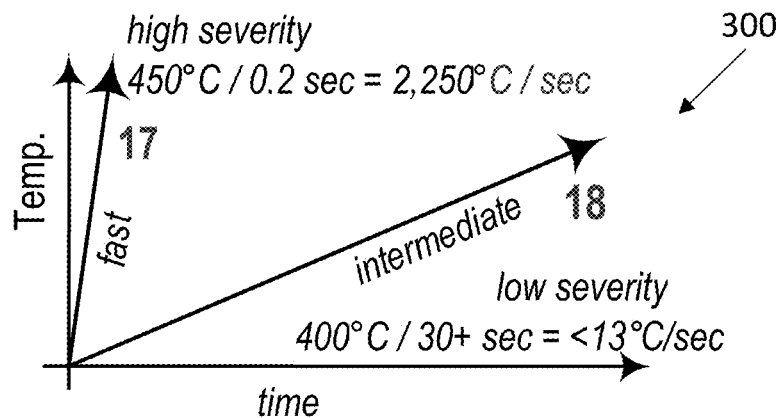
FIG. 5 is a schematic graphical depiction of temperature versus time comparing fast pyrolysis with intermediate pyrolysis.

As shown by the comparison chart 300 in FIG. 5, the heating rate in which these reactions take place are much less severe than fast pyrolysis 17, described in the background, which commonly reaches a few thousand degrees centigrade per second heat up rates and which may cause severe explosions of the structural nature of the lignocellulosic materials. In the systems and processes of the present disclosure, the structural nature of the lignocellulosic materials is maintained during the polysaccharide hydrodeoxygenation reactions due to the fact that the meso-pore sizes of this structure are similar to zeolite catalysts and therefore, behave in facilitating the reactions to alkanes. Therefore, an intermediate heat up rate 18 (longer than rate 17) as described in the embodiments of the present disclosure is used to enhance these reactions (e.g., ten seconds to several minutes). An intermediate heat up rate/ramp 18 of the present disclosure results in a low severity environment (low structural damage of the lignin based skeleton).

With continued reference to FIGS. 3-5, the ash elements of the resulting char are exposed as the lignocellulosic materials experience thermal degeneration. Some of these elements (e.g. iron, potassium, etc.) are known to contain active catalytic properties. These exposed active elements along with the skeleton char with a lattice structure similar in pore size to a zeolite catalyst help to promote the HDO reactions. A lower severity heat up in accordance with embodiments of the present disclosure allows the polysaccharides to volatize and react with the resident hydrogen in close proximity to the remaining lignin based skeleton (char). It should be noted that some of the volatilized polysaccharides will be trapped inside this skeleton and thus be discharged as high volatile solids (char) 131 to second reactor 130.

Figure 6:
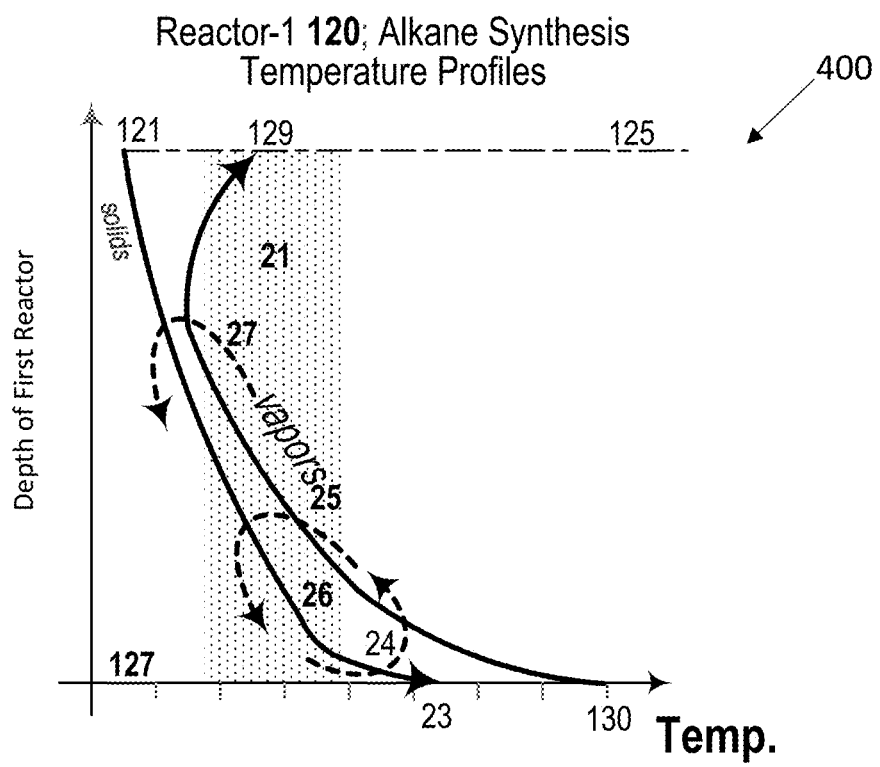
FIG. 6 is a schematic graphical depiction of temperature along the depth of the first reactor of the system of FIG. 1.

As shown in FIG. 6, the hydraulics and temperature control of first reactor 120 are shown in the temperature plot 400. Dry biomass 121 is fed to cold end 125 of first reactor 120. This solid biomass 121 will progress from cold end 125 to hot end 127 of first reactor 120, the gases and vapors percolate (indicated schematically by the arrows) through these solids in a counter flow orientation from the hot end proximate the entry of hot high-hydrogen concentration gas stream 139 from second reactor 130, to the cold end, proximate product gas 129. As the solids heat up, their polysaccharide components begin to volatilize 21 (the volatilization range is indicated schematically by the dotted pattern) at approximately 180-220° C. depending on the feedstock composition, and react with the hydrogen rich gases from second reactor 130. Some of the high molecular weight gases may condense 27 on the cooler solids and be recirculated to the hot end of first reactor 120. The condensation phenomenon progress to tars 25 as the solids continue progress through first reactor 120. The more severe the heating rate the higher the tars release rate. These condensates will crack and revolatilize off as lower molecular weight compounds 24 or be carried to the second reactor 130 at a temperature 23 just above the end of the cellulose volatilization temperature of 350° C.-400° C. depending on the feedstock composition. This condensation and revolatilization form a high recirculation load 26 within first reactor 120, thus increasing their residence time in the warmer sections of first reactor 120. The polysaccharide and hydrogen hydrodeoxygenation reactions are described above in relation to FIG. 4. Since hemicellulose and cellulose components volatilze, or react, at different temperatures, first reactor 120 tends to realize improved yields and lower tars by incorporating near isothermal zones.

Figure 7:
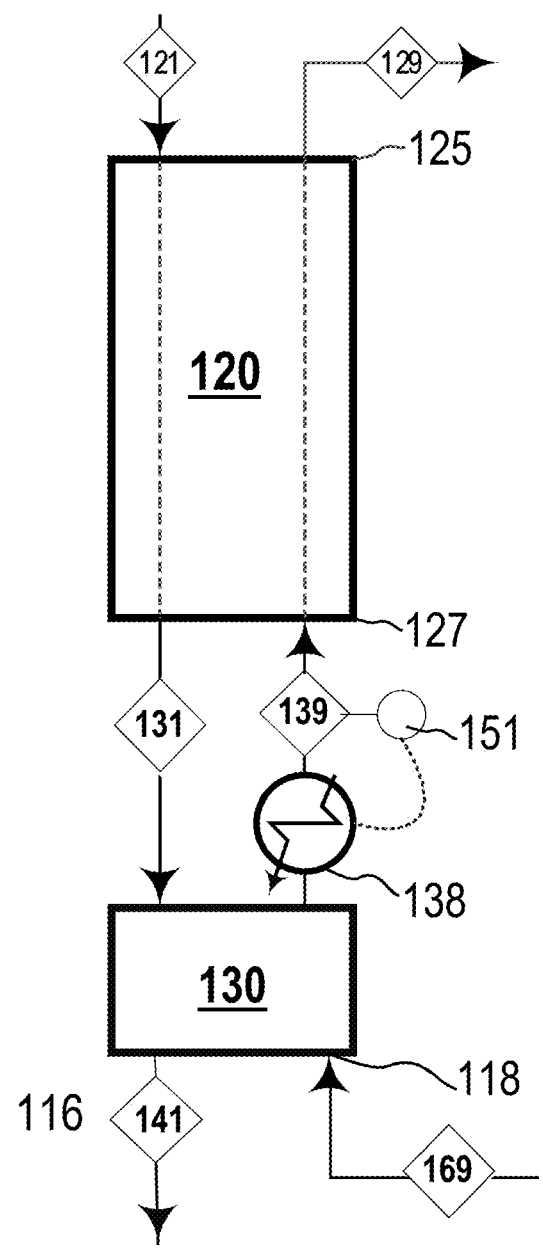
FIG. 7 is a schematic depiction of another embodiment of a reactor system for converting lignocellulosic feedstock into an alkane rich product constructed in accordance with the present disclosure, showing a first reactor with a first product stream output, a second reactor, and a gas cooler.

As shown in FIG. 7, it is also contemplated that in some embodiments of system 100, a thermal controller 138 is downstream from a first product outlet of the second reactor. The system 100 of FIG. 7 is substantially the same as system 100 of FIG. 1. In the embodiment of FIG. 7, thermal controller 138 is a gas cooler 138 which is used to control second reactor 130 hot high hydrogen concentration gas stream 139 temperature prior to it being introduced to the first reactor 120 to minimize explosive cracking of the feedstock polymers in hot end 127 of reactor 120. A temperature sensor 151 is operatively connected to thermal controller 138. Thermal controller 138 is between second reactor 130 and second inlet 106 of first reactor 120. In the embodiment of FIG. 7, second reactor 130 also includes a second inlet 118 upstream from the first product outlet. A relatively cooler feedstock 139, e.g. a hydrogen rich gas stream, may require supplemental, or recycled gas 169 from the distillation process or additional hydrogen producing feedstocks 169 (e.g. methane, waste lignin, etc.) to be provided to second reactor 130. This supplemental or recycled gas 169 allows for first reactor 120 to be controlled to optimize alkane production for different feedstocks. Second inlet 118 is configured and adapted to receive at least a portion of the distillation process recycle stream or supplemental gas 169 to maintain heat balance with the now cooled hydrogen rich pyrolysis gas stream 139.

Figure 8:
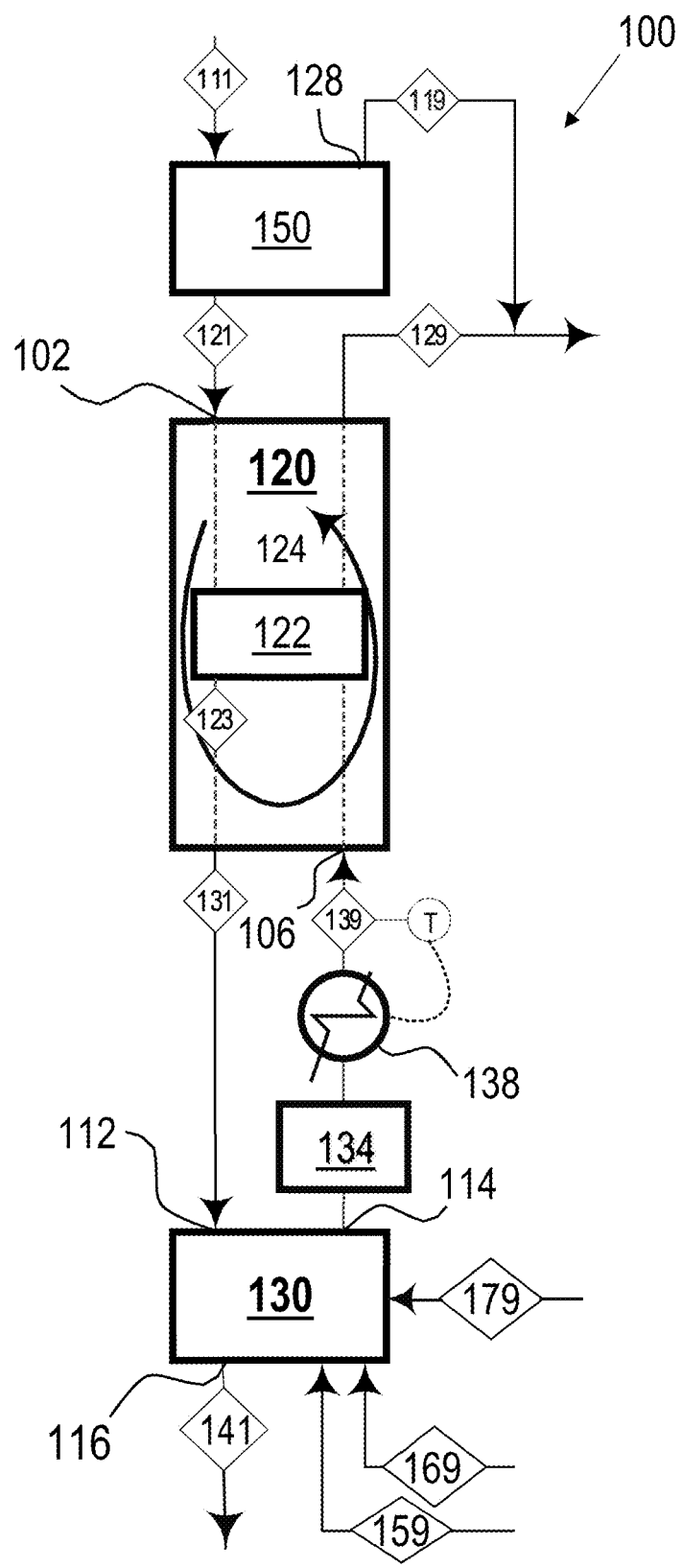
FIG. 8 is a schematic depiction of another embodiment of a reactor system for converting lignocellulosic feedstock into an alkane rich product constructed in accordance with the present disclosure, showing a lignocellulosic feedstock heater upstream from the first inlet of the first reactor.

As shown in FIG. 8, in another embodiment, system 100 includes a lignocellulosic feedstock heater 150 upstream from first inlet 102 of first reactor 120 to control the temperature of the lignocellulosic feedstock being input to first reactor 120 for the purpose of controlling the product gas 129 temperature and thus minimize the condensation of the high molecular weight (MW) product compounds from condensing on the cool feedstocks. System 100 of FIG. 8 is substantially similar to systems 100 of FIGS. 1 and 7. Heater 150 is configured and adapted to pre-heat an initial feed 111 of the lignocellulosic feedstock 121 being fed into first reactor 120 to temperatures up to 180° C. to control the product gas dew point by controlling stream 121 temperature to 100-230° C. (where stream 119 is the BTX [benzene, toluene, and xylenes] volatiles). Heater 150 includes a vent 128 in fluid communication with first product stream 129 to vent a potential volatiles stream 119 thereto. Heater 150 provides a drier and warmer lignocellulosic feedstock 121, as compared with initial feed 111. By controlling the temperatures of stream 121 at first inlet 102 and hot high-hydrogen concentration gas stream 139, a near isothermal zone 122 can be created (either by external gas recirculation, imbedded coils or fluid beds) just after the alkanation reaction (e.g. HDO reactions) zone 124 to enhance yields, and minimize tars liberation rates. Stream 123 schematically indicates where the high temperature begins to prefer pyrolysis over deoxygenation reactions.

System 100 in FIG. 8 also shows the addition of high temperature steam 159 to increase the amount of char cracked if hydrogen is needed in first reactor 120. Additionally, a portion of the unused distillation overs stream 169 is shown being recycled into second reactor 130 to increase both hydrogen concentration and mass of stream 139 to make heat balance on first reactor 120. The system 100 of FIG. 8 also includes a methane cracker 134 downstream from a first product outlet 114 of second reactor 130. Methane cracker 134 is between second reactor 130 and second inlet 106 of first reactor 120. Methane cracker 134 is added to react methane and water vapor to hydrogen and carbon monoxide, since both water vapor and methane inhibit the HDO reactions. System 100 of FIG. 8 also includes a stream 179 that provides other feedstocks, e.g. lignin, methane, or other organics materials, which would contribute to the increase of hydrogen and carbon monoxide production.

Figure 9:
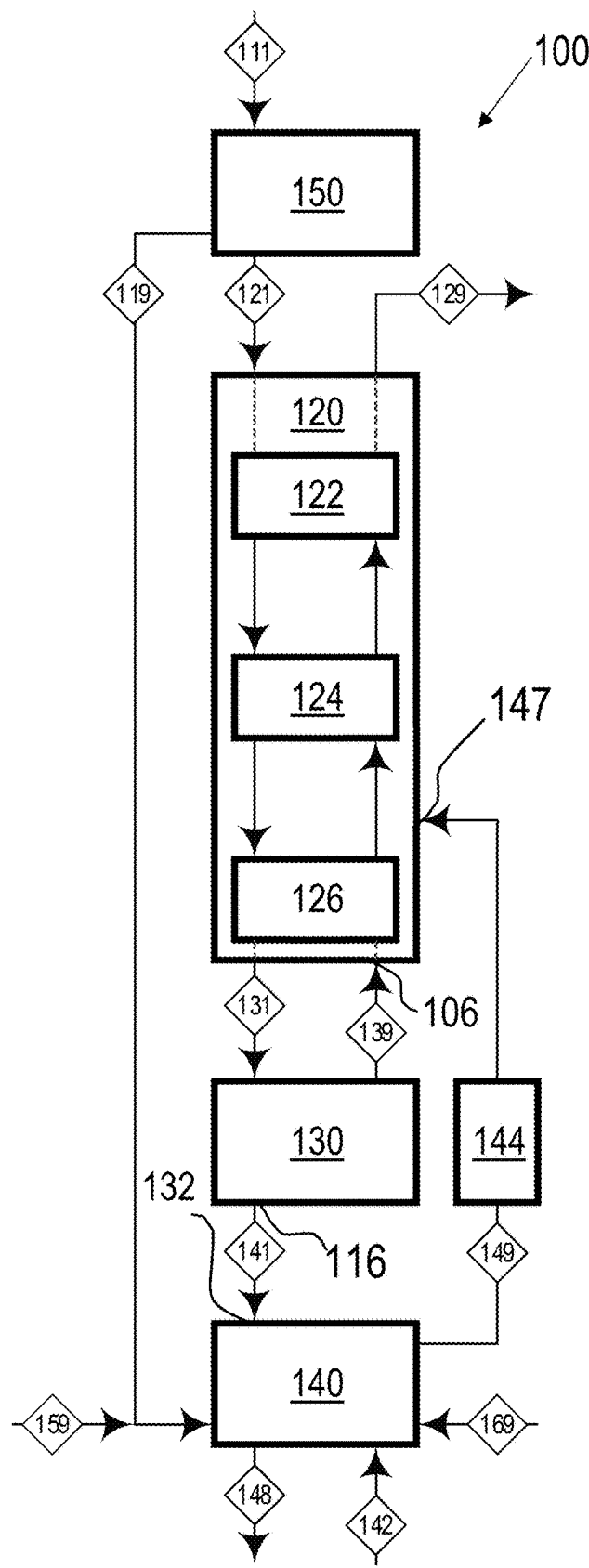
FIG. 9 is a schematic depiction of another embodiment of a reactor system for converting lignocellulosic feedstock into an alkane rich product constructed in accordance with the present disclosure, showing first, second and third reactors.
Figure 10:
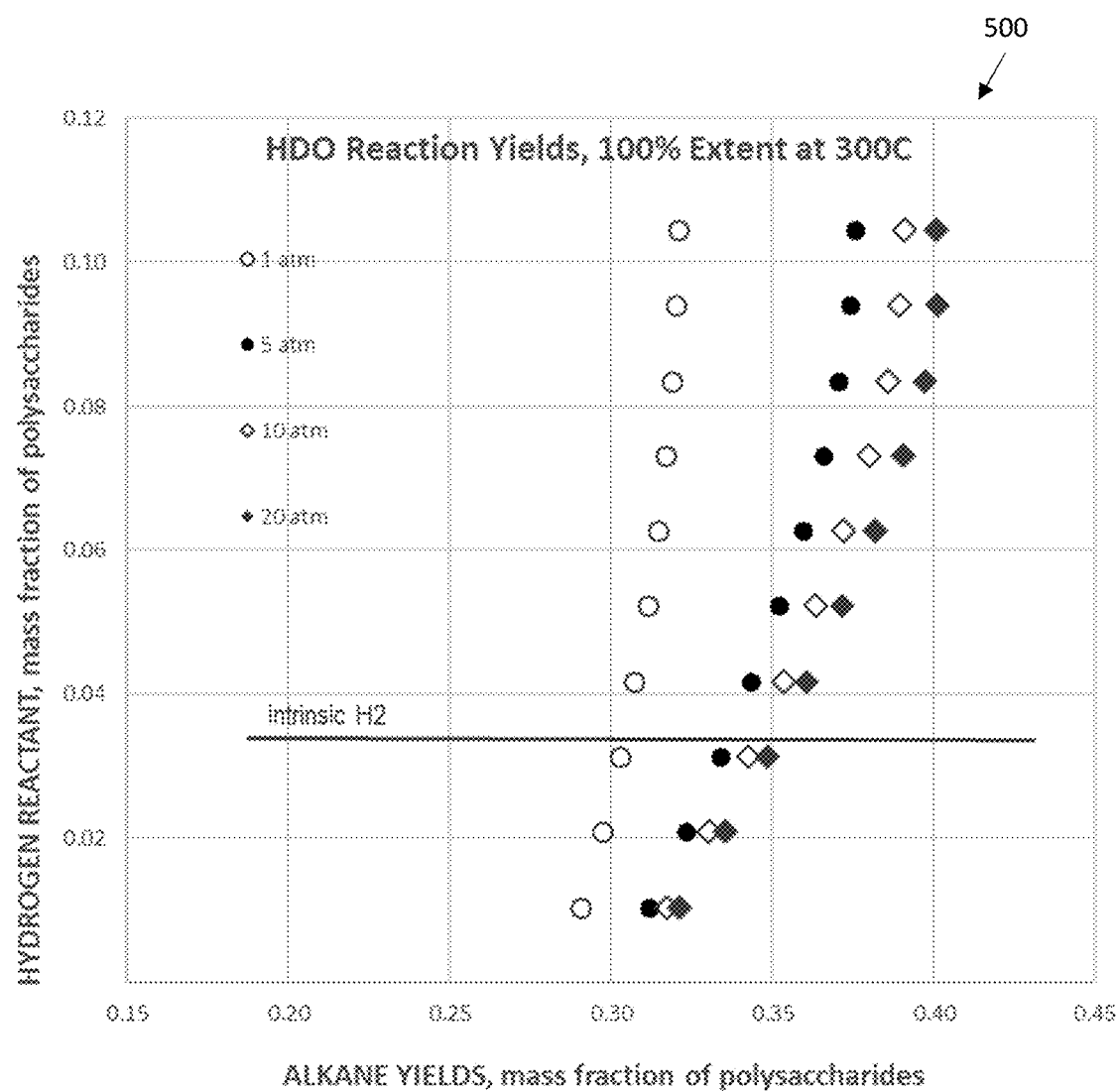
FIG. 10 is a schematic graphical depiction of the effect of pressure on HDO reaction yields in the first reactor.

With reference now to FIG. 9, a third reactor 140, e.g. a steam-carbon reactor, which uses high temperature steam (700+° C.), is included in system 100 of FIG. 9. System 100 of FIG. 9 is substantially the same as system 100 of FIGS. 1, 7 and 8, with a few differences readily visible in the figures and described below. FIG. 9 also shows the zones within first reactor 120 (which also readily apply to first reactor 120 of FIGS. 1, 7 and 9). The zones inside first reactor 120 include a zone 122 where high molecular weight gases condense onto the feed biomass 121, an alkanation reaction zone 124 where the bulk of the alkanation reactions occur, and a tar cracking zone 126. The alkanation reaction zone 124 typically ranges from 200° C. to 380° C. In accordance with some embodiments, zone 126 can be housed in a separate reactor discrete from reactor 120. This split arrangement may be desired when a large amount of tars are generated.

With continued reference to FIG. 9, system 100 includes a third reactor 140 downstream from second reactor 130. High temperature steam stream 159 and the unused distillation overs stream 169 are input into third reactor 140 for further processing (as opposed to second reactor 130 like in FIG. 8). Third reactor 140 includes a first inlet 132 in fluid communication with second product outlet 116 of second reactor 130 to receive an unused solids stream (char) 141 therefrom. Third reactor 140 produces additional hydrogen 149 from discharged char 141. The BTX volatiles stream 119, a steam stream 159, char 141 are recycled to third reactor 140 to form additional hydrogen 149. Hydrogen 149 is routed to a third inlet 147 of first reactor 120 at a position downstream from second inlet 106 and tends to reduce the tars generated in the hot end 127 of the reactor 120. Third reactor 140 includes a first output 145 in fluid communication with first reactor 120 via a third inlet 147 of first reactor 120 to provide additional hydrogen stream 149 thereto. In system 100 of FIG. 9, the volatiles stream 119 vents to third reactor 140, instead of back to product stream 129 like in FIG. 8. System 100 of FIG. 9 also includes a methane cracking catalyst unit 144 between third reactor 140 and first reactor 120. Methane cracking catalyst unit 144 reacts methane and water vapor to generate hydrogen and carbon monoxide products. The addition of recycled gas (or waste lignin spray) 169 acts to increase hydrogen production 139 in second reactor 130.

Those skilled in the art will readily appreciate that they systems and methods of the present disclosure provide increased yields (e.g. 20% higher), as compared with traditional processes such as those described in U.S. Pat. No. 9,382,482 to Weaver. Moreover, even where higher yields of Alkane product are not realized as compared to traditional systems and/or methods, the cost for the yield described herein is much less than those systems and methods that require expensive metal catalysts or large amounts of external fuels. It is contemplated that in some embodiments of the present invention, realized yields may be 75-85 gallons of alkane products per bone dry ton of lignocellulosic feedstock.

Examples—Stoichiometric and Gibbs Free Energy Minimization Simulation

Empirical stoichiometric calculations of the hydrodeoxygenation of a 5 carbon pentose result in nearly a 20% mass yield to pentane. However, the same 5 carbon pentose, exposed to a 0.026 weight percent of hydrogen, in a Gibbs Free Energy minimization simulation, results in nearly 24% mass yield to pentane at a pressure of 1 atmosphere and a temperature of 320° C. The same Gibbs Free Energy minimization simulation, with an additional 0.01 weight percent of carbon monoxide results in an almost 10% increase of pentane mass yields. Additionally, if the pressure in the Gibbs Free Energy minimization is increased to 5 atmospheres, the pentane mass yields increase to over 30%. This difference in yield between the example situations is due to the combined contribution of the hydrodeoxygenation reaction, carbon monoxide deoxygenation treatment of the polysaccharides, and pressure. Furthermore, the difference between the stoichiometric and the Gibbs Free Energy minimization simulation indicate that there are some pyrolysis gas reactions in the hot end, e.g. zone 126, of the reactor, where the pyrolysis volatiles are deoxygenating to alkanes in the high hydrogen, carbon monoxide atmosphere exposed to the catalytic effect of the reacting solids. Therefore, hydrodeoxygenation, carbon monoxide deoxygenation, pressure, and the catalytic effect of the reacting solids are all significant to converting the lignocellulosic materials to alkanes.

The methods and systems of the present disclosure, as described above and shown in the drawings, provide for systems and methods that convert lignocellulosic materials to alkanes which meet the ASTM specifications with minimal post processing (distillation and filtration). This is accomplished within a small footprint, without expensive precious metal catalysts or large amount of external fuels or hydrogen. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A process for converting lignocellulosic feedstock into an alkane rich product, the process comprising:
providing a lignocellulosic feedstock into a first inlet if a first reactor at a first end of the first reactor;
providing a hot feedstock into a second inlet of the first reactor at a second end of the first reactor;
heating and reacting the lignocellulosic feedstock with the hot feedstock;
outputting a first product stream from a first product outlet of the first reactor, wherein the first product stream is an alkane rich product stream;
outputting a second product from a second product outlet of the first reactor and feeding the second product into a second reactor;
heating the second product in the second reactor resulting in at least a hot high-hydrogen concentration gas stream; and
releasing the hot high-hydrogen concentration gas stream from the second reactor into the second inlet of the first reactor to provide at least a portion of the hot feedstock.

2. The process as recited in claim 1, wherein heating and reacting the lignocellulosic feedstock includes heating the lignocellulosic feedstock over a period ranging from 10 seconds to 20 minutes up to 400° C.

3. The process as recited in claim 1, wherein reacting the lignocellulosic feedstock with the hot feedstock includes a deoxygenation reaction between at least one of hydrogen ($H_2$) or carbon monoxide (CO), and polysaccharides.

4. The process as recited in claim 1, wherein the second product includes a volatile solid.

5. The process as recited in claim 1, wherein heating the second product in the second reactor includes heating the second product to a temperature over 700° C. resulting in the hot high-hydrogen concentration gas stream and an unused solids stream.

6. The process as recited in claim 1, further comprising discharging the unused solids stream from the second reactor.

7. The process as recited in claim 1, further comprising distilling the first product stream into an alkane rich liquid, aromatics, water, and gases.

8. The process as recited in claim 7, wherein 30%-50% of the alkane rich liquid of the first product stream comprises $C_{18}$ alkanes.

9. The process as recited in claim 7, wherein 30%-40% of the alkane rich liquid of the first product stream comprises $C_{16}$ and $C_{17}$ alkanes.

10. The process as recited in claim 1, wherein the first reactor is a counter-flow reactor configured and adapted to providing the hot feedstock in a counter-flow orientation relative to the lignocellulosic feedstock.

11. The process as recited in claim 1, further comprising cooling the hot feedstock with a thermal controller prior to providing the hot feedstock to the first reactor to minimize explosive cracking of polymers of the lignocellulosic feedstock.

12. The process as recited in claim 1, further comprising providing at least one of a recycled gas stream or a steam stream to the second reactor.

13. The process as recited in claim 1, further comprising pre-heating the lignocellulosic feedstock to a temperature up to 180° C. with a heater prior to providing the lignocellulosic feedstock to the first reactor.

14. The process as recited in claim 13, further comprising venting volatiles from the heater to a position downstream from the first product outlet of the first reactor.

15. The process as recited in claim 1, further comprising providing hydrogen to the first reactor at a position downstream from the second inlet of the first reactor.

16. The process as recited in claim 1, further comprising reacting methane and water vapor with a methane cracker to generate hydrogen and carbon monoxide products upstream from the second inlet of the first reactor.

17. A reactor system for converting lignocellulosic feedstock into an alkane rich product, the system comprising:
a first reactor having a first inlet at a first end, a second inlet at a second end and at least one product outlet, wherein the first reactor is configured and adapted to receive a lignocellulosic feedstock at the first inlet and a hot feedstock at the second inlet; and
a second reactor having a first inlet downstream from the at least one product outlet of the first reactor to receive a product therefrom, wherein the second reactor includes a first product outlet upstream from and in fluid communication with the second inlet of the first reactor to provide a hot high-hydrogen concentration gas stream thereto.

18. The system as recited in claim 17, wherein the second reactor includes a second product outlet configured and adapted to discharge an unused solids stream from the second reactor.

19. The system as recited in claim 17, wherein the first reactor is a counter-flow reactor configured and adapted to provide a hot feedstock in a counter-flow orientation relative to a lignocellulosic feedstock.

20. The system as recited in claim 17, further comprising a thermal controller downstream from a first product outlet of the second reactor, wherein the thermal controller is between the second reactor and the second inlet of the first reactor.

21. The system as recited in claim 17, wherein the second reactor includes a second inlet upstream from the first product outlet, wherein the second inlet is configured and adapted to receive at least one of a recycled gas stream or a steam stream.

22. The system as recited in claim 17, further comprising a heater upstream from the first inlet of the first reactor configured and adapted to pre-heat a lignocellulosic feedstock.

23. The system as recited in claim 22, wherein the heater includes a vent in fluid communication with the at least one product outlet of the first reactor configured and adapted to vent any potential volatiles stream.

24. The system as recited in claim 17, further comprising a third reactor downstream from the second reactor, the third reactor including a first inlet in fluid communication with a second product outlet of the second reactor to receive an unused solids stream therefrom, wherein the third reactor includes a first output in fluid communication with the first reactor via a third inlet of the first reactor to provide hydrogen thereto.

25. The system as recited in claim 17, further comprising a methane cracker downstream from a first product outlet of the second reactor, wherein the methane cracker is between the second reactor and the second inlet of the first reactor.

* * * * *